United States Patent [19]

Roy et al.

[11] Patent Number: 5,387,670

[45] Date of Patent: Feb. 7, 1995

[54] ANTIBIOTIC, DEOXYMULUNDOCANDIN, A PROCESS FOR ITS PRODUCTION AND ITS USE AS MEDICAMENT

[75] Inventors: Kirity Roy; Triptikumar Mukhopadhyay, both of Bombay, India; Hans-Wolfram Fehlhaber, Idstein; Herbert Kogler, Kelkheim, both of Germany; Bimal N. Ganguli, Bombay, India

[73] Assignee: Hoechst Aktiengesellschaft, Frankfurt am Main, Germany

[21] Appl. No.: 645,410

[22] Filed: Jan. 24, 1991

[30] Foreign Application Priority Data

Jan. 26, 1990 [EP] European Pat. Off. ......... 90101538

[51] Int. Cl.⁶ .................. A61K 37/02; C07K 5/12; C07K 7/06
[52] U.S. Cl. .................................................. 530/317
[58] Field of Search ..................... 530/317; 514/11

[56] References Cited

FOREIGN PATENT DOCUMENTS

0031662A1 7/1981 European Pat. Off. .
0031662 8/1981 European Pat. Off. .
0162032 3/1988 India .

OTHER PUBLICATIONS

Roy, et al, "Mulundocandin, A new Lipopeptide Antibiotic", J. of Antibiotics, pp. 275–281, 1987.
Chemical Abstract, vol. 111, 152145z.
CRC Handbook of Antibiotic Compounds, vol. IV, Part 1, Aminoacid and Peptide Antibiotics, pp. 355–368 (1980).
J. Antibiotics, 42:163–167 (1989) by Robert E. Schwartz et al.
J. Antibiotics, 42:168–173 (1989) by Carol F. Wichman, et al.

Primary Examiner—Robert J. Hill, Jr.
Assistant Examiner—S. G. Marshall
Attorney, Agent, or Firm—Finnegan, Henderson, Farabow, Garrett & Dunner

[57] ABSTRACT

Deoxymulundocandin, a compound of the formula I (SEQ. ID NO: 1)

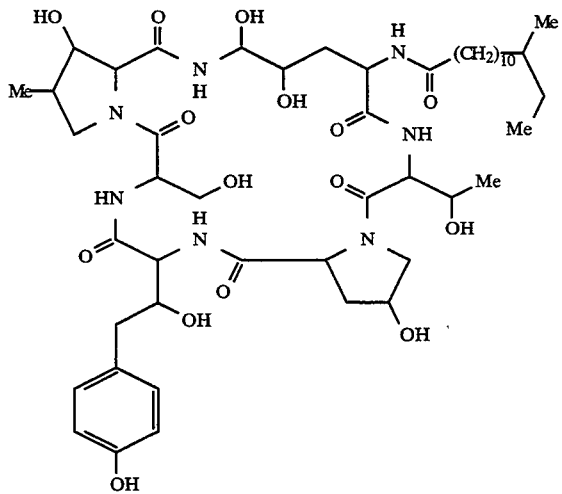

has an antiyeast, an antifungal and an immunomodulatory action.

3 Claims, 2 Drawing Sheets

ANTIBIOTIC, DEOXYMULUNDOCANDIN, A PROCESS FOR ITS PRODUCTION AND ITS USE AS MEDICAMENT

This invention relates to a novel antibiotic, Deoxymulundocandin, a process for its production and its use as medicament.

The antibiotic Deoxymulundocandin which has the following formula (SEQ. ID NO: 1)

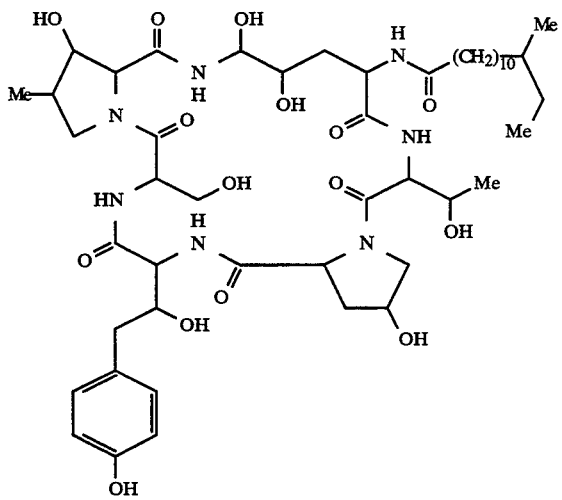

falls within the echinocandin type of antibiotics but is at the same time different from the known echinocandin type of antibiotics for the reasons stated hereinafter later. The echinocandin type of antibiotics are described in the 'CRC Handbook of Antibiotic compounds' Vol. IV, Part I, Amino Acid and Peptide Antibiotics, pages 355–368, Janos Berdy (Author), CRC Press, Inc., Boca Raton, Fla., U.S.A. 1980. Recently, similar antibiotics have been described in J. Antibiotics 42, 163–167 (1989) and J. Antibiotics 42, 168–173 (1989).

The instant invention also relates to obvious chemical equivalents and pharmaceutically acceptable derivatives of Deoxymulundocandin. The preparation of such derivatives is known for echinocandin type of antibiotics.

The echinocandin type of antibiotics are produced by several microorganisms belonging to the order Moniliales and the family Moniliaceae, for example, *Aspergillus nidulans, Aspergillus rugulosus, Aspergillus aculeatus, Aspergillus niger, Aspergillus nidulans-echinulatus, Aspergillus sydowii* (Bainier and Sattory) Thom and Church var. nov. mulundensis Roy (described in Indian Patent Application No. 162032 dated Feb. 3rd 1986) or *Acrophilophora luminispora*. The echinocandin type of antibiotics usually contains a natural peptide with a fatty acid side chain. The peptide portion consists of threonine, serine, hydroxyproline and several unusual amino acids. The fatty acid constituent could be linoleic, myristic or palmitic acid. The echinocandin type antibiotic has characteristic UV absorption at 225–226 and 276–278 nm and possesses antiyeast and antifungal activities and is usually of low toxicity.

An other object of the present invention is to provide a process for the production of a new antibiotic Deoxymulundocandin having the structure shown in formula I (SEQ. ID NO 1) from the microorganism *Aspergillus sydowdi* (Bainier and Sartory) Thom and Church var. nov. mulundensis Roy (Culture No. Y-30462) (described in Indian Patent Application No. 162032 dated 3rd Feb. 1986). Said microorganism has been deposited on Jan.15, 1990, according to the conditions of the Treaty of Budapest with Deutsche Sammlung von Mikroorganismen, Braunschweig (DSM 5745).

Figure 1:
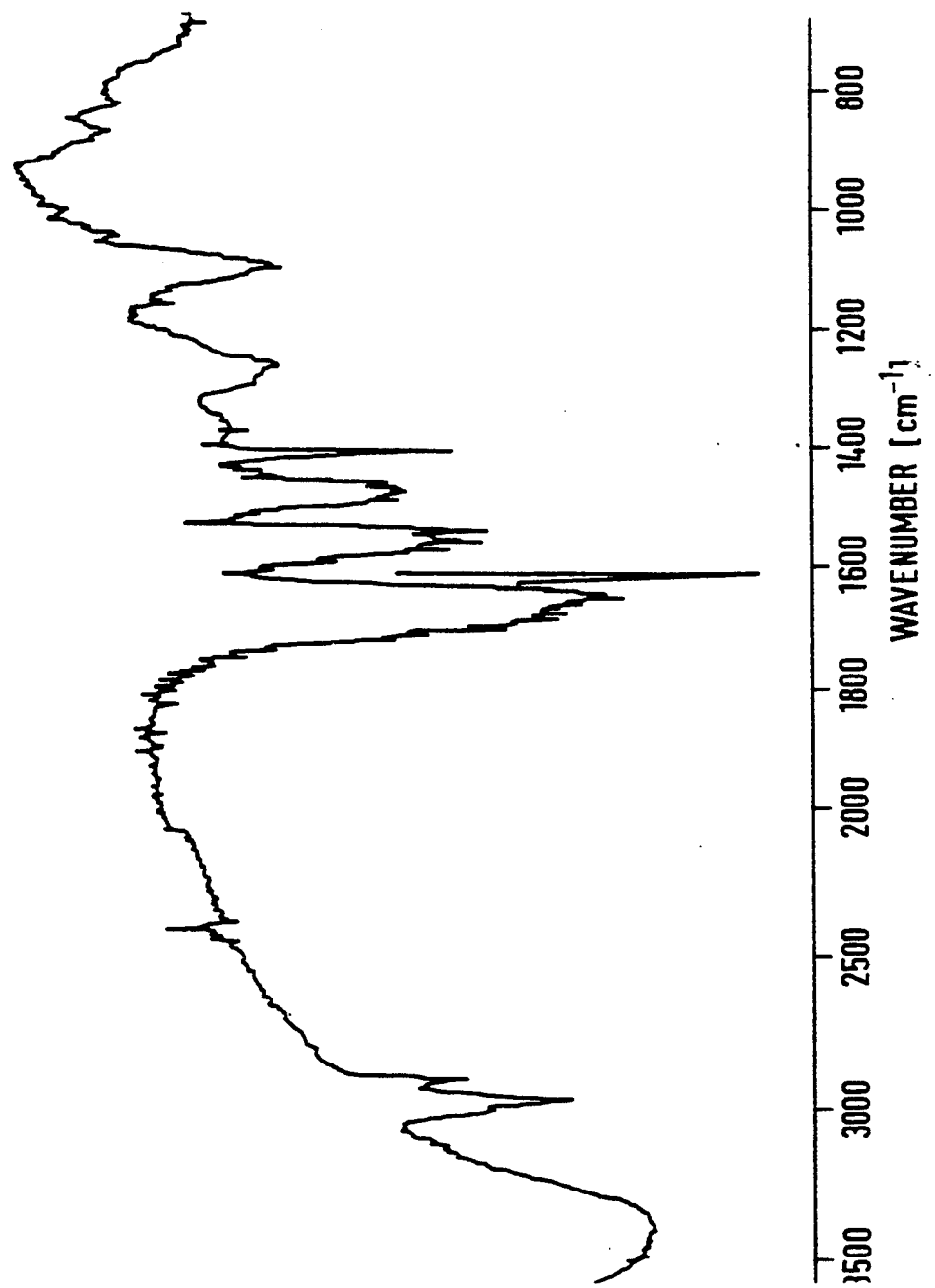
FIG. 1. IR spectrum (KBr) of deoxymulundocandin.

According to the present invention there is provided a process for the production of a new antibiotic Deoxymulundocandin having the above structure from a microorganism *Aspergillus sydowdii* (Bainer and Sartory) Thom and Church var. nov. mulundensis Roy (Culture No. Y-30462), (microorganism described in Indian Patent Application No. 162032 dated 3rd Feb. 1986), said process comprising cultivating the said microorganism by fermentation under aerobic conditions in a nutrient medium comprising carbon sources such as glucose or starch, nitrogen sources such as beef extract, tryprone or yeast extract and inorganic salts such as those of sodium, potassium, magnesium, calcium, iron, zinc, cobalt, manganese, copper, phosphorus or sulphur at a temperature between 25°–30° C. and pH 6–7 and isolating and purifying the said antibiotic from the culture broth in known manner.

If desired, the cultivation of culture No. Y-30462 is carried out in the presence of an antifoaming agent such as Desmophen ® (a linear polyether based on propylene oxide Bayer AG, Leverkusen, Germany). Preferably, the cultivation of culture No. Y-30462 is carried out at about 26° C. and pH about 6.5. The cultivation of culture No. Y-30462 is preferably carried out under submerged conditions and stopped at 66–80 hours. The new antibiotic in the culture fluid and the mycelium is detected by its activity tested against *Candida albicans* and *Saccharomyces cerevisiae* by the standard agar plate diffusion assay method (Assay method of antibiotics, a laboratory manual, 1955 by Grove, D. C. and Randall, W. A., Medical Encyclopaedia Inc. New York).

The following examples are illustrative of the present invention:

EXAMPLE I

Cultivation of the culture Y-30462 in shake flasks for the fermentative production of the antibiotic Deoxymulundocandin

| Composition of seed culture medium: | |
|---|---|
| Soyabean meal | 20.0 g |
| Glucose | 30.0 g |
| Calcium carbonate | 6.0 g |
| Sodium chloride | 3.0 g |
| Ammonium chloride | 2.5 g |
| Potassium dihydrogen phosphate | 2.0 g |
| Demineralised water | 1.0 liter |

The above seed culture medium was distributed in 100 ml wide mouth Erlenmeyer flasks and sterilised at 121° C. for 20 minutes. pH prior to autoclaving was 6.5. The flasks were cooled and inoculated with few loopfuls of a well sproulated culture of Y-30462 and shaken at 240 r.p.m. for 60 hours at 26° C. (±1° C.). This was used as seed culture for inoculating the production medium.

| Composition of production medium: | |
| --- | --- |
| Beef extract | 3.0 g |
| Tryptone | 5.0 g |
| Glucose | 10.0 g |
| Soluble starch | 24.0 g |
| Yeast extract | 5.0 g |
| Calcium carbonate | 4.0 g |
| Manganese chloride tetrahydrate | 0.5 mg |
| Zinc sulphate heptahydrate | 0.22 mg |
| Calcium chloride | 0.55 mg |
| Ferrous sulphate heptahydrate | 0.5 mg |
| Copper sulphate pentahydrate | 0.16 mg |
| Cobalt chloride hexahydrate | 0.16 mg |
| Demineralised water | 1.0 liter |

The above production medium was distributed in 200 ml amounts in 1 liter Erlenmeyer flasks and sterilised at 121° C. for 20 minutes. pH prior to autoclaving was 6.5. The flasks were cooled and then inoculated with the seed culture (1% v/v). The fermentation was carried out on a rotary shaker at 26° C. ($\pm 120$ C.) for 76 hours. After harvesting, the culture fluid was centrifuged and the new antiobiotic was isolated from both the mycelium and the filtrate as described in Example II.

EXAMPLE II

Cultivation of the culture Y-30462 in fermenters for the production of the new antibiotic Deoxymulundocandin Stage I: Preparation of seed culture (a) In shake flasks The seed culture medium 100 ml (as mentioned in Example I) was taken in 500 ml wide mouth Erlenmeyer flask with presterilisation pH adjusted to 6.5. This was sterilised in an autoclave at 121° C. for 20 minutes, cooled and inoculated with spores from the culture Y-30462. The flasks were incubated at 26° C. ($\pm 1°$ C.) for 48 hours at 240 r.p.m. on rotary shaker.

(b) In aspirator bottles 1 liter of the seed culture medium (as mentioned in Example I) was taken with 0.4 ml of Desmophen as antifoam in a 5 liter aspirator bottle. This was sterilised in an autoclave at 121° C. for 30 minutes, cooled and inoculated with spores from the culture Y-30462. The bottles were mounted on a rotary shaker and incubated for 48 hours at 26° C. ($\pm 1°$ C.) at 240 r.p.m.

Stage II: Fermentation (a) Small scale 10 liter of the production medium (as mentioned in Example I) with presterilisation pH adjusted to 6.5, with 4 ml Desmophen as antifoaming agent, in a 15 liter stainless steel fermenter was sterilised in an autoclave at 121° C. for 36 minutes, cooled under sterile positive air pressure in water bath and seeded with 1% seed under aseptic conditions.

This was run with the following parameters:

| Temperature | 26–27° C. |
| --- | --- |
| Aeration | 1:0.6 to 0.8 vol/vol. of broth |
| | 6 to 8 liters per minute |
| Agitation | 160 rpm |
| Harvest Time | 66 hours |

(b) Large Scale 95 liters of the production medium (as mentioned in Example I) in 150 liter fermenter with presterilization pH adjusted to 6.5 with 40 ml Desmophen or 270 liter medium in 390 liter fermenter with 75 ml Desmophen was sterilised in situ for 32 minutes at 121° C. and seeded with 1% seed under aseptic conditions.

Seeded volume: 110 liters in 150 liter fermenter 280 liters in 390 liter fermenter This was run with the following parameters:
Temperature: 26°–27° C.
Aeration: 1:0.6 to 0.8 vol/vol of broth
for 110 liters: 60 to 80 lpm
for 280 liters: 160 to 224 lpm (9 to 13 $nm^3$/hr)
Agitation: 100–110 r.p.m.
Harvest time: 66 hours The harvested broth was centrifuged to separate the mycelium from the culture liltrate and then processed further.

Stage III: Isolation of Deoxymulundocandin

Two culture broths—one from the 150 liter fermenter and another from the 390 liter fermenter—were combined and centrifuged to separate the culture filtrate from the mycelium (33.5 kg).

The culture filtrate (337 liters) was extracted once with ethyl acetate (245 liters). The mycelium (33.5 kg) was extracted with acetone ($2 \times 100$ liters) and the extract was concentrated to 60 liters at 38° C. under reduced pressure ($<100$ torr). The concentrate was diluted with 60 liters water and extracted with ethyl acetate ($4 \times 60$ liters). The extract was pooled with the culture filtrate extract. The combined ethyl acetate extract was concentrated at 38° C. under reduced pressure ($<100$ Torr) to obtain the crude antibiotic preparation as an oil (253 g). This was triturated with acetonitrile ($3 \times 5$ liters) and centrifuged. The clear solution was discarded and the residual solid was treated with methanol ($2 \times 1$ liter). After centrifugation the methanol solution was concentrated to obtain the semipure compound (6 g).

This compound was adsorbed on thin layer chromatography (TLC) grade silica gel and then loaded on to a column (3 cm$\times$85 cm) packed with TLC grade silica gel (350 g). The column which was packed in ethyl acetate was eluted under pressure at a flow rate of 20 ml/min with ethyl acetate: n-propanol (5:3) Deoxymulundocandin eluted out first followed by Mulundocandin and other bioactive compounds. The purity of the fractions were monitored by TLC (silica gel; developing solvent: EtOAc:n-propanol:$H_2O$ (5:3:1); detection-$I_2$ vapour) and the fractions containing only Deoxymulundocandin were combined. After removal of the solvent under reduced pressure pure compound (85 mg) was obtained.

Later fractions which were mixtures of Deoxymulundocandin and Mulundocandin were combined. Romoval of solvent under reduced pressure gave impure Deoxymulundocandin (440 mg).

Physicochemical Properties of the New Antibiotic Deoxymulundocandin

| 1. Appearance: | White amorphous powder |
| --- | --- |
| 2. Melting point: | 167–168° C. |
| 3. Solubility: | Soluble in methanol, dimethyl formamide, dimethyl sulfoxide, |

-continued

Figure 2:
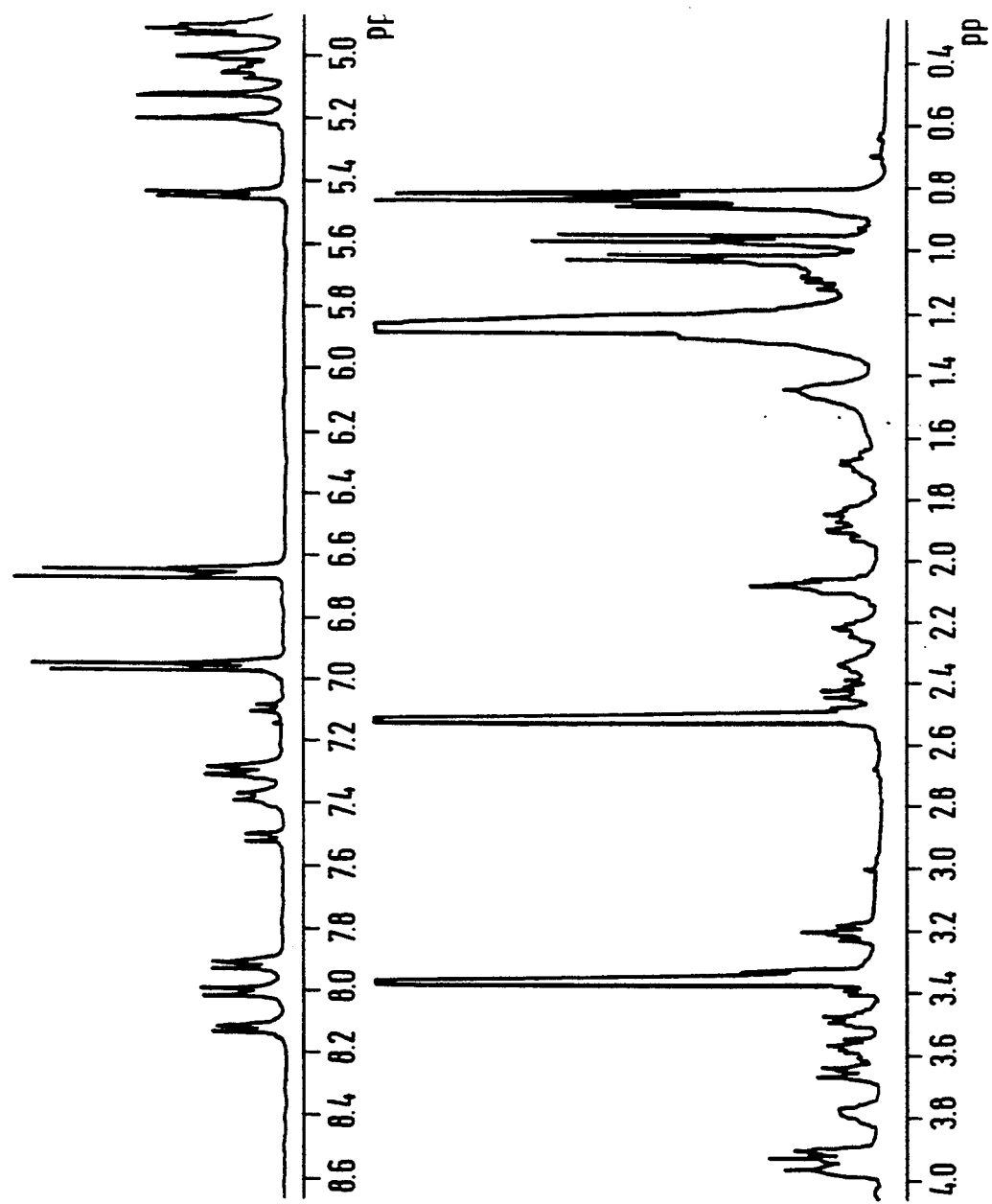
FIG. 2. 400 MHz $^1$H NMR spectrum of deoxymulundocandin.

| | | |
|---|---|---|
| | sparingly soluble in water, acetone, acetonitrile, ethyl acetate, carbon tetrachloride, chloroform, benzene, petroleum ether. | |
| 4. Colour reactions: (compound loaded on silica gel plate and sprayed) | Spray reagent KMnO$_4$ | Colour White in pink background |
| | FeCl$_3$/K$_3$Fe(CN)$_6$ | Blue in pale green background |
| | Ninhydrin | No characteristic colour |
| | Pauley's | No characteristic colour |
| | Ehrlich | No characteristic colour |
| | Benzidin-periodic acid | No characteristic colour |
| 5. $[\alpha]_D^{25}$: | −28.23° (c, 0.25, methanol) | |
| 6. Thin Layer Chromatography (on silica gel plate from E. Merck, item 5554) | Developing system EtOAc:n-PrOH: H$_2$O (5:3:1) | Rf 0.76 |
| | BuOH:AcOH:H$_2$O (4:1:1) | 0.71 |
| | CHCl$_3$:MeOH:17% Aqueous ammonia (2:2:1) Lower Layer | 0.58 |
| 7. High Pressure Liquid Chromatography | Retention Time 9.2 min | |
| Guard Column | 10 μ ODS Hypersil ® (3 cm × 0.4 cms) | |
| Column | 10 μ ODS Hypersil (25 cm × 0.4 cms) | |
| Eluent | MeOH:0.2% NaH$_2$PO$_4$,2H$_2$O in water:H$_3$PO$_4$ (75:25:0.1) | |
| Flow Rate | 2 ml/min | |
| 8. Molecular formula: | C$_{48}$H$_{77}$N$_7$O$_{15}$ (992.2) | |
| 9. Molecular weight: | confirmed by FAB-MS (matrix 3-nitrobenzylalcohol + lithium iodide); M + Li$^+$ found m/z 998.55, calculated 998.562 ($^{12}$C$_{48}$$^1$H$_{77}$$^{14}$N$_7$$^{16}$O$_{15}$$^7$Li). | |
| 10. UV spectrum: a) in MeOH: | λ max (E$_1$$^1$ $_{cm}$$^\%$) 225 (74), 276 (16.5), 282 sh (13.5) nm | |
| b) in MeOH/NaOH: (50 ul of 0.1N NaOH added to 3 ml MeOH solution) | 224 (72.5), 241 sh (37.5), 277 (15), 282 (14.5), 294 (8) nm | |
| 11. IR spectrum (KBr): | See FIG. 1 of the drawings accompanying the specification | |
| 12. 400 MHz $^1$H NMR spectrum | See FIG. 2 of the drawings accompanying the specification | |
| 13. Amino acid composition | 4-Hydroxyproline, serine, threonine, 3-hydroxy-4-methyl proline, 4,5-dihydroxyornithine and 3-hydroxyhomo-tyrosine. | |
| 14. Fatty acid composition | 12-Methyltetradecanoic acid | |

Thus the new antibiotic Deoxymulundocandin contains a fatty acid moiety which is 12-methyltetradecanoic acid. This fatty acid is found only in Mulundocandin and not in other echinocandin type antibiotics. However, the amino acid composition of Deoxymulundocandin is different from that of Mulundocandin. Deoxymulundocandin contains 3-hydroxyhomotyrosine and not 3,4-dihydroxyhomotyrosine which is present in Mulundocandin. As is clear from the physicochemical properties and the structure the new antibiotic Deoxymulundocandin is totally different from those of any known echinocandin type of antibiotic.

The new antibiotic Deoxymulundocandin has been found to possess antiyeast, antifungal and immunomodulatory properties. The minimum inhibitory concentrations of the new antibiotic Deoxymulundocandin required to inhibit different yeast and fungal strains have been found to be those given in Table I.

TABLE I

| Test Organisms | Minimum Inhibitory Concentration of the new antibiotic Deoxymulundocandin (SEQ ID NO: 1) in micrograms per milliliter |
| --- | --- |
| *Candida albicans* | 1.5 |
| *Saccharomycis cerevisiae* | 3.1 |
| *Aspergillus niger* | 3.1 |
| *Penicillium italicum* | 25 |
| *Cladosporium species* | 0.75 |
| *Cercospora beticola* 71 | 6.25 |
| *Botrytis cinerea* 47 | 6.25 |
| *Botrytis cinerea* 57 | 50 |
| *Botrytis cinerea* 211 | 25 |
| *Botrytis cinerea* 212 | 25 |
| *Trichophyton mentagrophytes* | <0.18 |
| *Microsporum gypseum* | 0.18 |
| *Microsporum canis* | <0.18 |

Accordingly, the instant invention also relates to pharmaceuticals which contain the compound of formula I (SEQ. ID NO: 1) or pharmaceutically acceptable derivatives thereof if appropriate together with customary auxiliaries and/or vehicles. Furthermore, the instant invention relates to the use of a compound of formula I (SEQ. ID NO: 1) or pharmaceutically acceptable derivatives thereof for the production of pharmaceuticals; details of the production are known from the literature which is concerned with echinocandin type of antibiotics.

as well as physiologically acceptable derivatives thereof.

2. A pharmaceutical composition comprising a compound as claimed in claim 1 in an amount effective to treat yeast infections and other fungal infections together with a physiologically acceptable vehicle.

We claim:

1. Deoxymulundocandin, a compound of the formula (SEQ. ID NO: 1)

3. A method for the treatment of yeast and other fungal infections in a host comprising the administration to said host of an anti-fungal effective amount of a compound as claimed in claim 1.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Xaa  Ser  Thr  Xaa  Xaa  Xaa
  1                  5